United States Patent [19]

Castelijns et al.

[11] Patent Number: 5,274,165
[45] Date of Patent: Dec. 28, 1993

[54] PROCESS FOR THE α-CHLORINATION OF PHENYLACETONITRILES

[75] Inventors: Anna M. C. F. Castelijns, Stein; Joannes M. C. A. Mulders, Geleen; Cornelis W. van den Broek, Landgraaf, all of Netherlands

[73] Assignee: DSM N.V., Heerlen, Netherlands

[21] Appl. No.: 894,430

[22] Filed: Jun. 5, 1992

[30] Foreign Application Priority Data

Jun. 7, 1991 [NL] Netherlands .................... 9100979

[51] Int. Cl.⁵ .................... C07C 253/30; C07C 255/35
[52] U.S. Cl. .................................................. 558/388
[58] Field of Search .......................................... 558/388

[56] References Cited

U.S. PATENT DOCUMENTS

| | | | |
|---|---|---|---|
| 2,302,228 | 11/1942 | Kharasch et al. | 570/197 X |
| 3,331,865 | 7/1967 | Weil et al. | 558/388 |
| 3,828,088 | 8/1974 | Shuman | 558/388 X |
| 3,880,927 | 4/1975 | Molloy | 564/366 |

FOREIGN PATENT DOCUMENTS 50-77323  6/1975  Japan .................... 570/197

OTHER PUBLICATIONS

Ohoka et al., "Reaction of Nitriles With Thionyl Chloride . . . ", Journal of Organic Chemistry, vol. 40, No. 24, 1975, pp. 3540–3544.
Hantzsch, "Uber Die Vermeintlichen . . . ", Berichte der Deutschen Chemischen Gesellschaft, vol. 64, 1931, pp. 667–678.

*Primary Examiner*—Joseph Paul Brust
*Attorney, Agent, or Firm*—Cushman, Darby & Cushman

[57] ABSTRACT

Process for the α-chlorination of phenylacetonitriles, for example benzyl cyanide, in which the phenylacetonitrile is contacted with a suitable chlorinating agent, sulphuryl chloride or chlorine gas, while an amount of strong acid, preferably HCl, is also present in the reaction mixture. The induction time and the reaction rate are dependent on, among other factors, the concentration of the acid. Preferably, the reaction is carried out under pressure. The reaction is well controllable.

16 Claims, No Drawings

PROCESS FOR THE α-CHLORINATION OF PHENYLACETONITRILES

The invention relates to a process for the α-chlorination of a phenylacetonitrile in which the phenylacetonitrile is contacted with sulphurylchloride or chlorine gas as chlorinating agent.

Such a process is known from Zhur. Obschei Khim. 28, 772 (1948). The process described here leads to a degree of conversion of 80.3%, relative to the amount of nitrile supplied, after one day's reaction. U.S. Pat. No. 3,880,927 also refers to this publication in connection with the preparation of β-phenyl-β,β-difluoroethylamines, which includes the chlorination of benzyl cyanide to α,α-dichlorophenylacetonitrile with the aid of sulphuryl chloride as an intermediate step.

Drawbacks of this process are that the chlorination does not start up until after an induction period, which is unpredictable per se, and that then, once the reaction has started up, it proceeds violently at first, forming an undesirably large amount of gas. Nevertheless, long reaction times are necessary for obtaining high degrees of conversion. As the reagents have all been introduced into the reactor, it is not possible to reduce the reaction rate once the reaction starts up and proceeds too violently, which, for safety reasons, makes it difficult to carry out the reaction on a large scale.

The aim of the invention is to provide a process in which the chlorination reaction starts up in a predictable manner and in which the development and the rate of the reaction can be controlled.

This is achieved according to the invention by contacting the phenylacetonitrile with a suitable chlorinating agent in the presence of an amount of strong acid.

A survey of the chlorination of aromatic compounds is given in for example the book by J. S. Pizey; Synthetic Reagents, Vol. 4, 336-396 (1981). It is assumed that the side-chain chlorination of aromatic compounds under the influence of sulphuryl chloride usually proceeds via a radical mechanism and is accelerated by (UV) light and radical initiators such as peroxides. It is for example known that in the absence of peroxide the side-chain chlorination of toluene, which is in such reactions comparable with phenylacetonitrile, under the influence of sulphuryl chloride does not take place. Only after the addition of for example benzoyl peroxide does a reaction take place. A further indication of the fact that the side-chain chlorination of aromatic cyanides most probably takes place via a radical mechanism is the photochlorination of benzyl cyanide with the aid of $Cl_2$ gas to the α-monochlorobenzyl cyanide as described in the literature (Chem. Zentrallblatt (1927) II, 415). Nucleus chlorination of aromatic compounds on the other hand takes place via an ionogenic mechanism and these chlorinations are catalysed by for example Lewis acids (such as $AlCl_3$ and $FeCl_3$). In addition, the same survey mentions that the chlorination of alkylnitriles cannot be carried out effectively with the aid of sulphuryl chloride. It is also known that acetonitrile and chloroacetonitrile do not react with an equivalent amount of sulphuryl chloride at room temperature after 24 hours (Wijman D. P., Kaufman P. R., Freeman W. R.; J. Org. Chem. 29 2706 (1964)).

The applicant has now found that the use of radical initiators in the chlorination of benzyl cyanide with the aid of sulphuryl chloride does not lead to a clearly observable acceleration of the reaction and that on the other hand a strong acid unexpectedly functions as a catalyst in these reactions, which means that a long induction time is avoided and the reaction rate is increased simply by ensuring the presence of a strong acid. In the known process for the chlorination of a phenylacetonitrile the catalytic effect of a strong acid is not recognised. These preparation processes are effected under atmospheric conditions. The reason why long reaction times are necessary is to be found in the fact that the HCl concentration of the reaction mixture gradually decreases due to evaporation as the reaction proceeds. In the process according to the invention the reaction is preferably carried out under pressure to make a higher HCl concentration possible.

The presence of sufficient strong acid ensures an instantaneous reaction of the substrate and the chlorinating agent without an induction time. This makes it possible to control the development of the reaction via the supply of the substrate and/or the chlorinating agent. Moreover, it has been found that the side-chain chlorination proceeds with a very high selectivity and that, contrary to what has been found for the chlorination of alkylnaphthalenes with the aid of sulphuryl chloride (see GB-A-263844), no chlorination of the nucleus whatsoever takes place. No undesired byproducts are hence formed in the reaction. In compounds which contain two H atoms at the α position the monochlorinated product appears to chlorinate faster than the non-chlorinated starting material, because at every moment during the reaction there is virtually no monochlorinated product in the reaction mixture.

The chlorination of saturated alkylnitriles with the aid of chlorine gas in the presence of HCl is described in the publication J. Gen. Chem. USSR 25, 905-906 (1955), in which it is proposed that the chlorination proceeds according to an ionogenic reaction mechanism. In view of the fact that it is generally proposed that the side-chain chlorination of aromatic compounds proceeds via a radical mechanism, one would not expect HCl gas to be a suitable catalyst for the side-chain chlorination of phenylacetonitriles, particularly as HCl is usually considered to be a catalyst for reactions that proceed via an ionogenic mechanism and lead to nucleus chlorination. It was therefore by no means to be expected that a process for the chlorination of alkylnitriles as described in J. Gen. Chem. USSR 25, 905-906 (1955) could be used for the selective side-chain chlorination of aromatic compounds. This is also confirmed by the great amount of time that has passed since the latter publication, in which not a single suggestion has been made in the direction of the present process. See for example the aforementioned, more recent publications U.S. Pat. No. 3,880,927 of 1975 and Pizey's book of 1981.

With the process according to the invention phenylacetonitriles in the side-chain are chlorinated. For example, benzyl cyanide is chlorinated to α,α-dichlorophenylacetonitrile. The phenylacetonitriles may optionally be substituted in the nucleus and/or may contain one substituent in the side chain.

Examples of such compounds are:

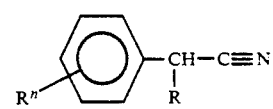

where:

n=1-5 and $R^n$ may each individually be H, an alkyl, aryl, alkoxy, a halogen or

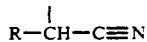

and R is H, an alkyl, aryl, alkoxy or a halogen. The alkyl and alkoxy groups in $R^n$ and R may contain 1-6 C atoms; the aryl group may optionally be substituted with one or more substituents chosen from the group comprising alkyl with 1-6 C atoms, alkoxy with 1-6 C atoms and halogen.

Such compounds are for example suitable intermediates in the preparation of end products such as the rubber promoters described in U.S. Pat. No. 4,435,552 or the β-phenyl-β,β-difluoroethylamines as described in U.S. Pat. No. 3,880,927.

As a suitable chlorinating agent use is made of sulphurylchloride ($SO_2Cl_2$) or chlorine gas ($Cl_2$) which are the chlorinating agents that are usually used for such reactions. In the case of less stable substrates use is preferably made of sulphuryl chloride because then, in comparison with for example chlorine gas, less stringent conditions can be used.

If the stability of the substrate imposes no limitations the use of chlorine gas is preferable for economic reasons, on account of its lower cost price. Moreover, the use of chlorine gas presents the advantage, in comparison with for example sulphuryl chloride, that no $SO_2$ is released as a byproduct, which means that, finally, less salt ends up in the environment.

The order in which the reagents are supplied is not critical. In practice, the chlorinating agent is usually added to the substrate. Preferably, the chlorinating agent is supplied during the reaction, which limits the loss thereof. In addition, the development of the reaction can be well controlled in this manner via the supply rate.

As a catalyst use can in principle be made of all strong acids for example Brönsted acid that are inert with respect to the reaction, for example p-toluene sulphonic acid, naphion H, polyphosphoric acid, HCl, HBr or mixtures thereof. Preferably, use is made of HCl because this acid is formed during the chlorination reaction and is hence not foreign to the process. The catalyst can be added as such or can be generated in situ.

The amount of strong acid in the reaction mixture may vary within wide limits; usually, it is 0.005-1.0 mole of strong acid per mole of nitrile. The minimum amount of acid is for example dependent on the temperature and the pressure of the reaction mixture. A person skilled in the art can easily determine the optimum concentration of strong acid.

If the acid concentration at the beginning of the reaction is high enough, no induction period will ensue. If the acid concentration at the beginning of the reaction is low, an induction period will ensue, which is dependent on the concentration of the acid. The amount of acid present in the reaction mixture is hence chosen so that no or only a very short induction period will ensue, so that no high concentrations of the two reagents occur before the reaction starts up because in that case the development of the reaction would be uncontrollable. Preferably, the strong acid is already present in the reaction mixture before a start is made with the dosing of the chlorinating agent or the substrate. Moreover, the greater the amount of strong acid in the reaction mixture, the higher the reaction rate. During the reaction sufficient HCl is usually formed to keep the acid concentration at the required level. Optionally, additional acid may be added at the end of the reaction, when only little substrate remains in the reaction mixture, as a result of which the reaction rate decreases and little HCl is formed. This is done to correct for any loss of acid, so that the reaction rate remains at a relatively high level. If the reaction is effected under atmospheric pressure, the strong acid is hence preferably at least partially supplied in the course of the reaction.

The process according to the invention may be carried out with or without a solvent that is inert in the chlorination reaction. Preferably, the reaction is carried out without a solvent because then the greatest production capacity and the simplest procedure for further processing is obtained.

In a preferred embodiment of the process according to the invention the phenylacetonitrile is supplied and brought to the reaction temperature without a solvent. Then HCl gas is supplied, after which the chlorinating agent is supplied at such a rate that conversion of the chlorinating agent instantaneously ensues.

The reaction can be carried out under atmospheric conditions or under elevated pressure, such as 0.1-15 MPa, preferably 0.2-1 MPa. Preferably, the reaction is carried out under pressure to enable the use of a higher HCl concentration. This makes it possible to maintain a higher HCl concentration in the reaction mixture throughout the entire reaction, as a result of which the reaction rate also increases. In addition, this makes it possible to further increase the reaction rate by carrying out the reaction at a higher temperature, without causing great losses of chlorinating agent ($SO_2Cl_2$), while sufficient HCl remains present as a catalyst to maintain a high reaction rate. Moreover, it has been found that when the reaction is carried out under pressure only very little HCl is required to initiate the reaction, after which sufficient HCl is generated and remains in solution to keep the reaction rate high. When use is made of for example $SO_2Cl_2$, traces of $H_2O$ in the apparatus or the reagents are already capable of generating sufficient HCl to initiate the reaction. The temperature will usually be between 0° and 100° C., preferably between 30° and 60° C. In practice, the temperature and pressure will be chosen so that sufficient chlorinating agent and acid remain in solution.

The invention will now be elucidated with the aid of the following examples without, however, being limited thereto.

COMPARATIVE EXPERIMENT A 1161 grams of benzyl cyanide (99%; 9.8 mole) and 3052 g of $SO_2Cl_2$ (99%; 22.4 mole) are successively introduced into a double-walled glass reactor vessel with a volume of 8 liters, fitted with a bottom discharge, baffles, a stirrer and a reflux condenser. The reaction mixture is heated to 40° C. with stirring. After 6 hours the reaction starts up, which is apparent from the violent formation of gas. The temperature is maintained at 40° C. throughout the reaction. After 30 hours no gas formation is observable any more and the reaction mixture is drained (1857.5 grams), sampled and analysed by means of gas chromatography (GC).

91% of the benzyl cyanide is converted with a selectivity towards α,α-dichlorobenzyl cyanide of 96% and a selectivity towards α-monochlorobenzyl cyanide of 0.1%. The incomplete conversion of benzyl cyanide is due to the loss of $SO_2Cl_2$ from the reactor as a result of evaporation/entrainment.

EXAMPLE I 604.5 g of benzyl cyanide (99%; 5.1 mole) and 1587 grams of $SO_2Cl_2$ (99%; 11.6 mole) are successively introduced into a double-walled glass reactor vessel with a volume of 3.5 liters, fitted with a bottom discharge, baffles, a stirrer, a reflux condenser and a gas feed tube. The reaction mixture is heated to 40° C. with stirring and immediately after 14 grams of dry HCl gas (HCl/CN=0.075) is supplied in 30 minutes. After all of the HCl gas has been supplied the reaction starts up within 2 minutes, which is apparent from the observable formation of gas. The temperature is kept at 40° C. throughout the reaction. After 21 hours no gas formation is observable any more and the reaction mixture (962.1 grams) is drained and analysed by means of GC. 88% of the benzyl cyanide is converted with a selectivity towards $\alpha,\alpha$-dichlorobenzylcyanide of 97% and a selectivity towards $\alpha$-monochlorobenzyl cyanide of 0.1%. The incomplete conversion of benzyl cyanide is attributable to the loss of $SO_2Cl_2$ from the reactor due to evaporation/entrainment.

COMPARATIVE EXPERIMENT B 980 grams of benzyl cyanide (99%; 8.3 mole) is introduced into a double-walled glass reactor vessel with a volume of 3.5 liters, fitted with a bottom discharge, baffles, a stirrer, a reflux condenser and a dropping funnel, and is then heated to 30° C. Then 2630 g of $SO_2Cl_2$ (99%; 19.3 mole) is supplied, with stirring, at a rate of 220 g/hour (dosing time=12 hours). After 1.5 hours violent gas formation suddenly ensues. The dosing is temporarily stopped and is resumed after about 10 minutes. The development of the reaction is followed by means of gas chromatography. After 4 hours, 8 hours, 12 hours, 24 hours and 31 hours the degree of conversion of the benzyl cyanide is 13.7%, 35.3%, 77%, 96.7% and 99%, respectively. The selectivity towards $\alpha,\alpha$-dichlorobenzyl cyanide is 99%.

EXAMPLE II 980 grams of benzyl cyanide (99%; 8.3 mole) is introduced into a double-walled glass reactor vessel with a volume of 3.5 liters, equipped with a bottom discharge, baffles, a stirrer, a reflux condenser, a gas feed tube and a dropping funnel, and is heated to 30° C. Then 31 grams of HCl gas is introduced in 30 minutes. Immediately after the supply of 2630 grams of $SO_2Cl_2$ (99%; 19.3 mole) is started, with stirring, at a rate of 220 g/hr (dosing time=12 hours). After about 15 minutes the reaction starts up, as is apparent from the formation of gas. The development of the reaction is followed by means of gas chromatography. After 4 hours, 8 hours, 12 hours, 24 hours and 31 hours the degree of conversion of the benzyl cyanide is 32%, 62%, 84%, 96% and 99%, respectively. The selectivity towards $\alpha,\alpha$-dichlorobenzyl cyanide is 99%.

EXAMPLE III 988.5 grams of benzyl cyanide (99%; 8.36 mole) is introduced into a cylindrical double-walled reactor vessel with a volume of 2.8 liters, fitted with an impeller stirrer, a reflux condenser, a pressure control, a thermocouple, a sampling point, an $SO_2Cl_2$ dosing system and a gas feed tube. The reaction vessel is then purged using $N_2$. The maximum pressure of the reactor is set to 4 bar with the aid of the pressure control. The reactor contents are heated to 30° C., after which 40.5 grams of HCl gas is supplied in 5 minutes, with stirring. Then, the supply of 2510 grams of $SO_2Cl_2$ (99%; 18.4 mole), at a rate of 436.5 grams/hour (dosing time=5.75 hours), is started, with stirring, while the temperature of the reaction mixture is maintained at 30° C. and the pressure in the reactor at 4 bar. Within 10 minutes after the start of the dosage of $SO_2Cl_2$ the reaction starts up. The development of the reaction is followed in time by means of gas chromatography. 1 hour, 2 hours, 4 hours and 8 hours after the start of the dosage of $SO_2Cl_2$ the degree of conversion of the benzyl cyanide is 19%, 38%, 73% and 99.9%, respectively. The selectivity towards $\alpha,\alpha$-dichlorobenzyl cyanide is quantitative.

EXAMPLE IV 988.5 grams of benzyl cyanide (99%; 8.36 mole) is introduced into a cylindrical double-walled reaction vessel with a volume of 2.8 liters, fitted with an impeller stirrer, a reflux condenser, a pressure control, a thermocouple, a sampling point, an $SO_2Cl_2$ dosing system and a gas feed tube. The reaction vessel is purged using $N_2$. The maximum pressure of the reactor is set to 4 bar with the aid of the pressure control. The reactor contents are heated to 50° C., after which 5 grams of HCl gas is supplied in 1 minute, with stirring. Then the supply of 2510 grams of $SO_2Cl_2$ (99%; 18.4 mole), at a rate of 1091.3 grams per hour (dosing time=2.3 hours), is started, with stirring, while the temperature of the reaction mixture is maintained at 50° C. and the pressure in the reactor at 4 bar. Within 10 minutes after the start of the supply of the $SO_2Cl_2$ the reaction starts up. The development of the reaction is followed in time by means of gas chromatography. 1 hour, 2 hours, 4 hours and 5 hours after the start of the supply of $SO_2Cl_2$ the degree of conversion of the benzyl cyanide is 48%, 90%, 99.6% and 100%, respectively. The benzyl cyanide is quantitatively converted to $\alpha,\alpha$-dichlorobenzyl cyanide.

COMPARATIVE EXPERIMENT C 80 grams of benzyl cyanide (99%; 0.68 mole) is introduced into a cylindrical reaction vessel with a volume of 250 ml, fitted with 4 baffles, a stirrer, a reflux condenser and a gas feed tube. The reaction vessel is then purged using $N_2$. The reactor contents are heated to 40° C., after which dry $Cl_2$ gas is introduced at a rate of 6 liters per hour. After 45 minutes a temperature effect is observed (40°→45°) and gas is formed.

Then the supply rate of the $Cl_2$ gas is increased to 8-9 liters/hour, while the temperature of the reaction mixture is maintained at 40° C. 4.5 hours after the start of the supply of the $Cl_2$ slipthrough of $Cl_2$ gas is observed and the supply rate of the $Cl_2$ gas is reduced to 2-3 liters/hour. The development of the reaction is followed by analysing samples taken in time by means of GC. After 1.5 hours, 3 hours and 5 hours the degree of conversion of the benzyl cyanide is 17%, 54% and 62%, respectively. After a reaction time of 4 hours the reaction rate decreases considerably. The benzylcyanide is converted virtually quantitatively into $\alpha,\alpha$-dichlorobenzyl cyanide.

EXAMPLE V 80 grams of benzyl cyanide (99%; 0.68 mole) is introduced into a cylindrical reaction vessel with a volume of 250 ml, fitted with 4 baffles, a stirrer, a reflux condenser and two gas feed tubes. The reaction vessel is then purged using $N_2$.

The reactor contents are heated to 40° C., after which dry HCl gas is introduced in 45 minutes, at a rate of 8-9 liters/hour. Then the supply of $Cl_2$ gas at a rate of 6-7 liters/hour is started. The chlorination reaction starts up immediately. The temperature of the reaction mixture is maintained at 40° C. After 4 hours slipthrough of $Cl_2$ gas is observed and the supply rate of the $Cl_2$ gas is reduced to 1 liter/hour.

The development of the reaction is followed by analysing samples taken in time by means of GC. After 1 hour, 3 hours and 5 hours the degree of conversion of the benzyl cyanide is 24%, 73% and 85%, respectively. The benzyl cyanide is converted virtually quantitatively into $\alpha,\alpha$-dichlorobenzyl cyanide.

EXAMPLE VI 80 grams of benzyl cyanide (99%; 0.68 mole) is introduced into a cylindrical reaction vessel with a volume of 250 ml, fitted with 4 baffles, a stirrer, a reflux condenser and two gas feed tubes. The reaction vessel is then purged using $N_2$.

The reactor contents are heated to 40° C., after which dry HCl gas is introduced at a rate of 8-9 liters/hour. After 45 minutes the supply rate of the HCl gas is reduced to 2-3 liters/hour and the supply of dry $Cl_2$ gas, at a rate of 10 liters/hour, is started. The chlorination reaction starts up immediately. After a reaction time of 1 hour and 45 minutes slipthough of $Cl_2$ gas is observed and the supply rate of the $Cl_2$ gas is reduced to 5-6 liters/hour. The development of the reaction is followed by analysing samples taken in time by means of GC. After 1 hour, 3 hours, 5 hours and 6 hours the degree of conversion of the benzyl cyanide is 44%, 80%, 88% and 91%, respectively. The benzyl cyanide is converted virtually quantitatively into $\alpha,\alpha$-dichlorobenzyl cyanide.

EXAMPLE VII 80 grams of benzyl cyanide (99%; 0.68 mole) is introduced into a cylindrical reaction vessel with a volume of 250 ml, fitted with 4 baffles, a stirrer, a reflux condenser and a gas feed tube. The reaction vessel is then purged using $N_2$. The reactor contents are heated to 40° C., after which 1.2 grams of p-toluenesulphonic acid is added ($H^+/CN=0.01$).

Then the supply of dry $Cl_2$ gas, at a rate of 8-9 liters/hour, is started. The chlorination reaction starts up immediately. The temperature of the reaction mixture is maintained at 40° C. After 15 minutes the supply rate of the $Cl_2$ gas is reduced to 6-7 liters/hour. The development of the reaction is followed by analysing samples taken in time by means of GC. After 2 hours and 4 hours the degree of conversion of the benzyl cyanide is 36.5% and 69.5%, respectively. The benzyl cyanide is converted virtually quantitatively into dichlorobenzyl cyanide.

EXAMPLE VIII 10 grams of $\alpha$-methylbenzyl cyanide (99%; 0.076 mole) dissolved in 70 grams of $\alpha,\alpha$-dichlorophenylacetic ethyl ester is introduced into a cylindrical reaction vessel with a volume of 250 ml, fitted with 4 baffles, a stirrer, a reflux condenser and two gas feed tubes. The reaction vessel is then purged using $N_2$. The reactor contents are heated to 40° C., after which HCl gas is introduced at a rate of 8-9 liters/hour. After 1 hour the supply rate of the HCl gas is reduced to 2-3 liters/hour and the supply of dry $Cl_2$ gas, at a rate of 6-7 liters/hour, is started. The chlorination reaction starts up immediately. After a reaction time of 40 minutes slipthrough of $Cl_2$ gas is observed and the supply rate of the $Cl_2$ gas is reduced to 4 liters/hour. The development of the reaction is followed by analysing samples taken in time by means of GC. After 1 hour, 2.5 hours and 3.5 hours the degree of conversion of the $\alpha$-methylbenzyl cyanide is 5.5%, 14.5% and 20%, respectively. The $\alpha$-methylbenzyl cyanide is converted virtually quantitatively into $\alpha$-chloro-$\alpha$-methylbenzyl cyanide.

EXAMPLE IX 15 grams of p-methylphenylacetonitrile (99%; 0.11 mole) dissolved in 60 grams of $\alpha,\alpha$-dichlorophenylacetic ethyl ester is introduced into a cylindrical reaction vessel with a volume of 250 ml, fitted with 4 baffles, a stirrer, a reflux condenser and two gas feed tubes. The reaction vessel is then purged using $N_2$. The reactor contents are heated to 40° C., after which HCl gas is introduced at a rate of 8-9 liters/hour. After 1 hour the supply rate of the HCl gas is reduced to 2 liters/hour and the supply of dry $Cl_2$ gas, at a rate of 6-7 liters/hour, is started. The chlorination reaction starts up immediately. The development of the reaction is followed by analysing samples taken in time by means of GC. After 1 hour, 2 hours, 4 hours and 5 hours the degree of conversion of the p-methylphenylacetonitrile is 45.5%, 64.5%, 78.5% and 84.5%, respectively. The p-methylphenylacetonitrile is converted virtually quantitatively into $\alpha,\alpha$-dichloro(p-methylphenyl)acetonitrile.

We claim:

1. Process for the $\alpha$-chlorination of a phenylacetonitrile in which the phenylacetonitrile is contacted with sulphurylchloride or chlorine gas as chlorinating agent in a liquid phase reaction, in the presence of a catalytically effective amount of an inert strong acid sufficient to promote chlorination of the phenylacetonitrile exclusively on the side-chain.

2. Process according to claim 1 wherein a Brönsted acid is used as a strong acid.

3. Process according to claim 1 wherein phenylacetonitrile is used as a starting material.

4. Process according to claim 1 wherein the chlorinating agent is supplied to the phenylacetonitrile.

5. Process according to claim 4, wherein at least part of the strong acid is supplied before the supply of the chlorinating agent is started.

6. Process according to claim 1 wherein the reaction is carried out under atmospheric pressure and at least part of the strong acid is supplied in the course of the reaction.

7. Process according to claim 7, wherein HCl is used as the Brönsted acid.

8. Process for the $\alpha$-chlorination of a phenylacetonitrile in which the phenylacetonitrile is contacted with sulphurylchloride or chlorine gas as chlorinating agent in a liquid phase reaction under an elevated pressure.

9. Process according to claim 8, wherein a catalytically effective amount of an inert strong acid sufficient to promote chlorination of the phenylacetonitrile exclusively on the side-chain is supplied to the reaction.

10. Process according to claim 9, wherein Brönsted acid is used as a strong acid.

11. Process according to claim 10, wherein HCl is used as the Brönsted acid.

12. Process according to claim 8, wherein phenylacetonitrile is used as a starting material.

13. Process according to claim 8, wherein the chlorinating agent is supplied to the phenylacetonitrile.

14. Process according to claim 9, wherein at least part of the strong acid is supplied before the supply of the chlorinating agent is started.

15. Process according to claim 9, wherein at least part of the strong acid is supplied in the course of the reaction.

16. Process according to claim 1, wherein the acid is introduced into the reaction mixture prior to contacting with either the chlorinating agent or the phenylacetonitrile.

* * * * *